United States Patent
Srivastava et al.

(10) Patent No.: US 9,040,688 B2
(45) Date of Patent: May 26, 2015

(54) INTERMEDIATES IN THE PREPARATION OF 1,4-DIPHENYL AZETIDINONE

(75) Inventors: Dhananjai Srivastava, Pune (IN); Rajiv Kumar Shakya, Pune (IN); Namrata Anil Chaudhari, Pune (IN); Inamus Saqlain Ansari, Pune (IN); Girij Pal Singh, Pune (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 588 days.

(21) Appl. No.: 13/260,877

(22) PCT Filed: Mar. 31, 2010

(86) PCT No.: PCT/IN2010/000214
§ 371 (c)(1),
(2), (4) Date: Sep. 28, 2011

(87) PCT Pub. No.: WO2010/113182
PCT Pub. Date: Oct. 7, 2010

(65) Prior Publication Data
US 2012/0029185 A1    Feb. 2, 2012

(30) Foreign Application Priority Data
Mar. 31, 2009 (IN) .............................. 562/KOL/2009

(51) Int. Cl.
*C07D 205/08* (2006.01)
*C07D 263/22* (2006.01)
*C07D 205/04* (2006.01)

(52) U.S. Cl.
CPC ............ *C07D 263/22* (2013.01); *C07D 205/04* (2013.01); *C07D 205/08* (2013.01)

(58) Field of Classification Search
CPC ........................... C07D 205/04; C07D 205/08
USPC ................................................. 540/200, 356
See application file for complete search history.

(56) References Cited

U.S. PATENT DOCUMENTS

| 5,767,115 A | 6/1998 | Rosenblum et al. |
| 5,856,473 A | 1/1999 | Shankar |
| 5,886,171 A | 3/1999 | Wu et al. |
| 6,207,822 B1 | 3/2001 | Thiruvengadam et al. |
| RE37,721 E | 5/2002 | Rosenblum et al. |

FOREIGN PATENT DOCUMENTS

WO    WO 2007/119106    10/2007

OTHER PUBLICATIONS

Greene et al., *Protective Groups in Organic Synthesis*, Third Edition, John Wiley & Sons, Inc., 1999, pp. V, 292-297, 355-359, and 724-727.
"Database HCPLUS", XP002598047, 1984, pp. 1-8.
International Search Report from International Application No. PCT?IN2010/000214 mailed Sep. 9, 2010.
Oare et al., "Stereochemistry of the Michael Addistion of N,N-Disubstituted Amide and Thioamide Enolates to α,β-Unsaturated Ketones", *Journal of Organic Chemistry*, vol. 55, 1990, pp. 132-157.
Rosenblum et al., "Discovery of a-(4-Fluorophenyl)-(3R)-{3-(4-fluorophenyl)-(3S)-hydroxypropyl}-(4S)-(4-hydroxyphenyl)-2-azetidinone (SCH 58235): A Designed, Potent, Orally Active Inhibitor of Cholestrol Absorption", *J. Med. Chem.*, vol. 41, 1998, pp. 973-980.

*Primary Examiner* — Golam M M Shameem
*Assistant Examiner* — Laura Daniel
(74) *Attorney, Agent, or Firm* — Merchant & Gould P.C.

(57) ABSTRACT

The process of the present invention relates to a method for the synthesis of a 1,4-diphenylazetidinone of formula (VIII) by using novel oxime intermediates.

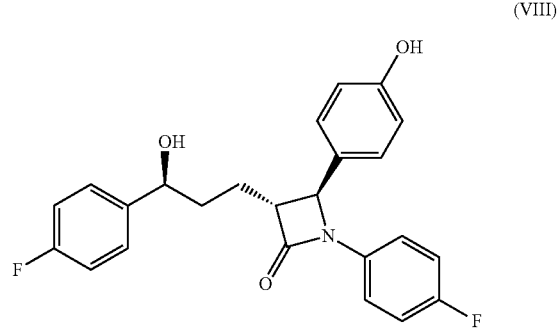

(VIII)

9 Claims, No Drawings

INTERMEDIATES IN THE PREPARATION OF 1,4-DIPHENYL AZETIDINONE

TECHNICAL FIELD OF THE INVENTION

This application is a National Stage Application of PCT/IN2010/000214, filed 31 Mar. 2010, which claims benefit of Serial No. 562/KOL/2009, filed 31 Mar. 2009 in India and which applications are incorporated herein by reference. To the extent appropriate, a claim of priority is made to each of the above disclosed applications.

The present invention relates to a novel synthetic process for the preparation of a 1,4-diphenylazetidinone.

BACKGROUND OF THE INVENTION

The azetidinone of the below formula, which is the subject of the present invention, is a

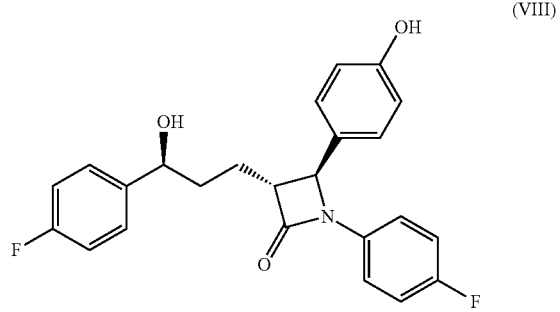 [SMILES: O=C1[C@H](CC[C@H](O)c2ccc(F)cc2)[C@@H](c2ccc(O)cc2)N1c1ccc(F)cc1]

(VIII)

therapeutically useful compound. It is disclosed in the product patent RE37721, which is a re-issue of U.S. Pat. No. 5,767,115. Different processes for its synthesis are also described therein.

This compound is a biologically active molecule and research has shown it to have the useful property of inhibiting the absorption of cholesterol from the intestine (*J. Med. Chem.* 1998, 41(6), 973). Since then this azetidinone—1-(4-fluorophenyl)-3(R)-[3(S)-hydroxy-3-(4-fluorophenyl)propyl)]-4(S)-(4-hydroxyphenyl)-2-azetidinone—has been approved by the USFDA and other regulatory authorities worldwide for use in the lowering of cholesterol in humans. It is at present marketed under the names of Zetia™, Ezetrol™, Ezemibe™, Zient™ et cetera.

Many processes for the preparation of this cholesterol absorption inhibitor have been reported: most are total chemical synthesis and others have a few enzymatic steps. The product patent itself discusses various synthetic strategies. In general, the difference in the routes lies in the introduction of the 4-fluorophenyl group, which is at the end of the aliphatic side-chain, with respect to the formation of the azetidinone ring. The azetidinone ring is obtained by cyclization, which could be carried out after the three substituted-phenyl groups have been incorporated into the molecule. However, in an alternate method the same cyclization may be carried out first and then the 4-fluorophenyl group at the end of the side chain or, sometimes, the whole side chain is attached onto this ring. In the processes described in U.S. Pat. No. 6,207,822 and WO2007/119106 the 4-fluorophenyl moiety is part of the molecule which is then cyclized to form the 4-membered ring, whereas, U.S. Pat. No. 5,886,171 and U.S. Pat. No. 5,856,473 describe processes wherein the 4-fluorophenyl group is introduced later.

Of these two strategies, it has been observed that within the former approach also there are two different methods that revolve around the secondary hydroxyl group. In the synthesis of this 1,4-diphenylazetidinone, the hydroxyl group is always brought in by the reduction of the corresponding ketone. In certain processes the reduction of the ketone to form the alcohol is done in the first step itself, while in others the reduction to alcohol is preferred in the final stages. However, regardless of whether the reduction is carried out initially or later in the synthesis, the moiety therein has to be protected in order to avoid the formation of by-products that lead to lowering in the yield of the desired product. When reduction is done at the beginning then the resulting alcohol is protected by a suitable protecting group and if done later, then the pro-moiety, i.e. the ketone, is protected suitably.

The process that forms the present invention too follows the former strategy wherein the molecule comprising the three substituted phenyl groups is cyclized to create the azetidinone ring. Further, the ketone moiety on the side chain is protected until formation of the β-lactam ring and then deprotected and reduced stereospecifically to yield the desired product.

OBJECT OF THE INVENTION

Herein we report novel intermediates in the synthesis of this 1,4-diphenyl azetidinone. In one aspect is presented the novel intermediate of formula (II).

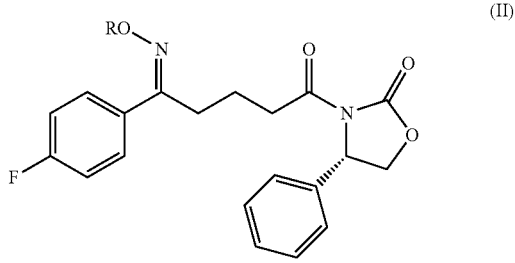

(II)

The novel intermediate of formula (IV) forms the second aspect of this invention.

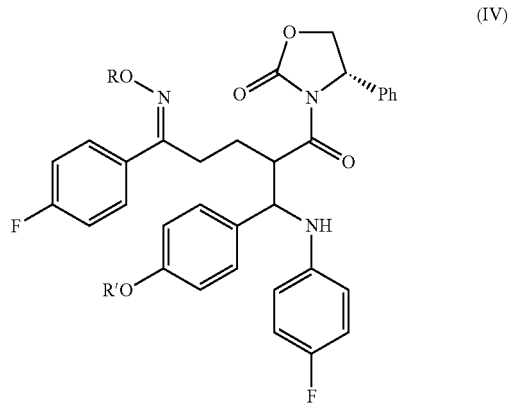

(IV)

In the third aspect is presented the intermediate of formula (V).

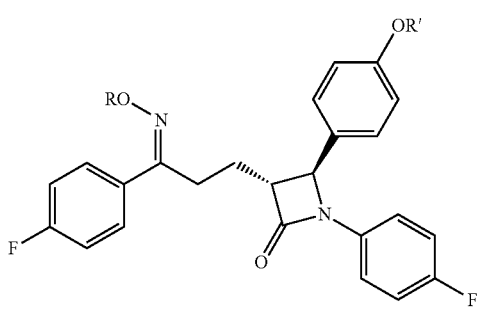

(V)

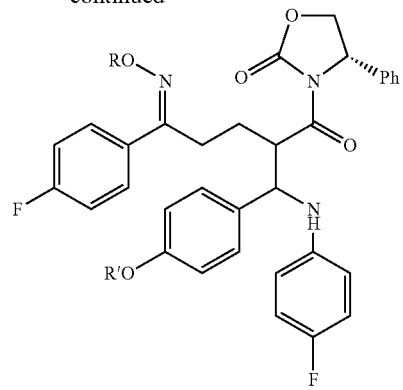

R' = H, protecting group
(IV)

The fourth aspect of this invention is a novel process for the synthesis of the 1,4-diphenyl azetidinone of formula (VIII).

In a fifth aspect is provided a chemical process for the synthesis of 1,4-diphenyl azetidinone of formula (VIII), using the above intermediates and thereby minimizing the loss in yield.

The intermediate of formula (IV) is a β-(substituted-amino) amide which is cyclized in the following steps to form the azetidinone ring. The resulting compound is also a novel intermediate of formula (V).

SUMMARY OF THE INVENTION

The present process for the synthesis of 1-(4-fluorophenyl)-3(R)-[3(S)-hydroxy-3-(4-fluorophenyl)propyl)]-4(S)-(4-hydroxyphenyl)-2-azetidinone involves the condensation of an imine of formula (III) with a ketone of formula (I), wherein the ketone functionality is protected as an oxime of formula (II). Thus, the compounds of formula (III) and (II) are reacted to give a novel compound of formula (IV).

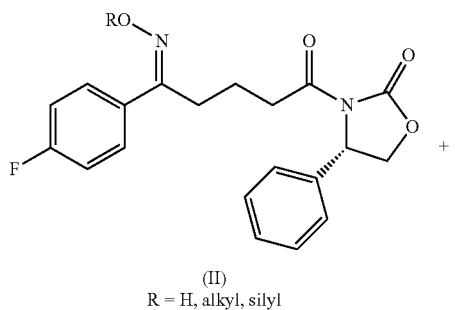

(II)
R = H, alkyl, silyl

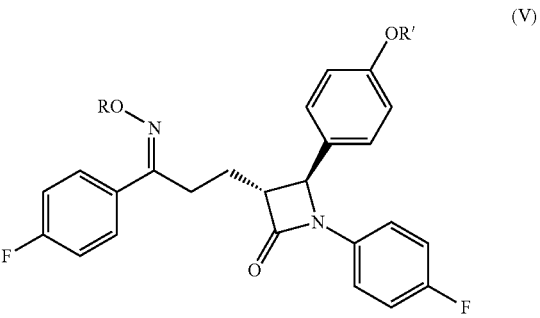

(V)

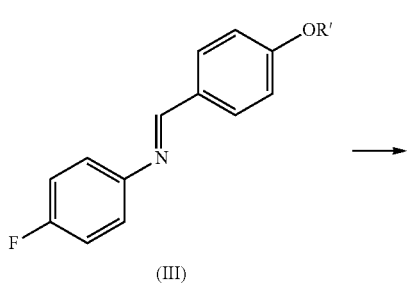

(III)

The steps that follow involve the deprotection of the ketone group, (i.e. removal of the oxime functionality), reduction of the resulting ketone and deprotection of the phenolic protecting group to obtain the desired final product.

This process has been developed for manufacture on a large scale and the parameters of economy of synthesis, excellent yield and ease of operation can be ascribed to it. The full details of the process are presented below.

DESCRIPTION

As mentioned hereinabove, the present synthesis follows the widely used strategy of incorporating the three substituted-phenyl groups into the chiral compound of formula (IV), which is then cyclized to form the azetidinone. The reaction scheme is as shown below.

SYNTHETIC SCHEME

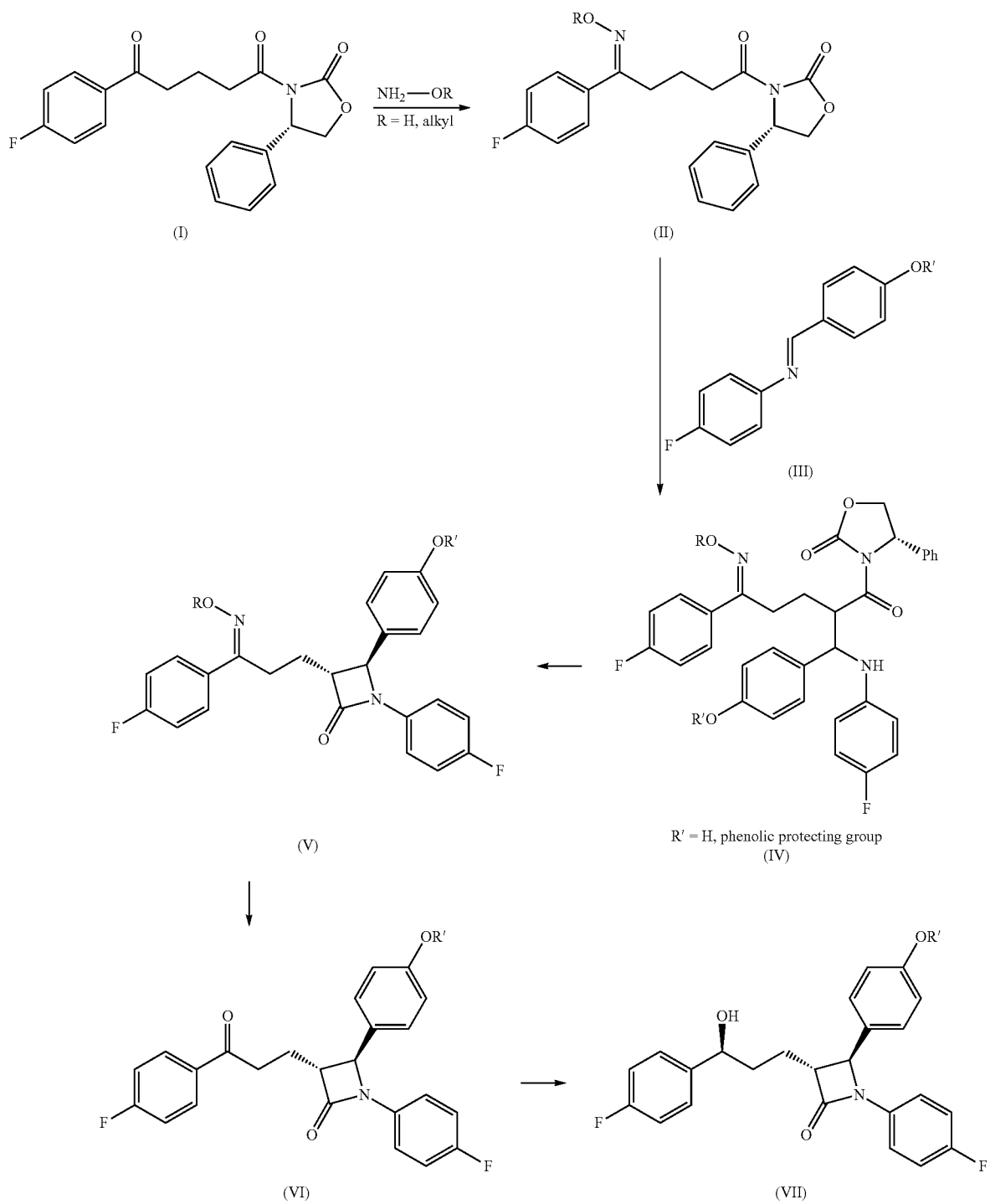

The synthesis begins with the compound of formula (I). In most instances this is the preferred starting material and can be prepared by any suitable means of synthesis. Thus the ketone (I), comprising the 4-phenyloxazolidinone chiral auxiliary, is treated with a hydroxylamine or its O-alkyl derivative to protect the ketone as an oxime. The starting material can be dissolved in any suitable solvent, preferably an alcohol, and is reacted with a hydroxylamine or its derivative. The reaction is carried out in the presence of a base, wherein an inorganic or an organic base may be used. Periodic sampling to determine the amount of unreacted ketone could be done in order to determine reaction completion. However the reaction was found to be complete after 8-12 hours.

If hydroxylamine is used to make the oxime, then the free hydroxyl group of the oxime may be optionally protected. Any suitable hydroxyl protecting group could be used such as an alkyl or silyl protecting group and this compound may be taken forward for further reactions.

The oxime (II) can be carried forward for further steps. When the oxime was isolated it was found to exist predominantly as the E-isomer. 92.6% E-isomer for the oxime formed with O-methyl hydroxylamine. However, for purposes of this invention, as the oxime

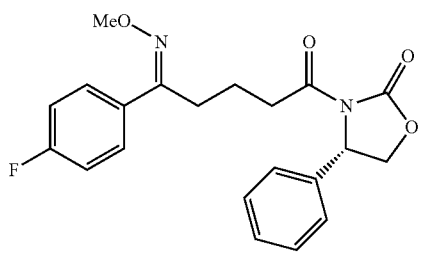 [SMILES: CO/N=C(/CCCC(=O)N1C(=O)OC[C@@H]1c1ccccc1)c1ccc(F)cc1]

only serves to protect the ketone functionality, the percentage of E/Z isomers is immaterial to the present synthesis. Accordingly the separation of these isomers is not envisaged and both isomers are taken forward for subsequent steps in the manufacturing process.

The oxime is then reacted with the imine (III), wherein the phenolic group is protected by any suitable protecting group known in the art, to form the β-substituted amino amide (IV). This reaction is carried out in the presence of $TiCl_4$ and Titanium isopropoxide in any suitable solvent. Preferred solvents are dichloromethane and methyl tertiary butyl ether (MTBE). The product obtained is then treated with N,O-bis (trimethylsilyl)acetamide (BSA) and tetrabutylammonium fluoride (TBAF) in a solvent medium to form the β-lactam ring. The solvent medium that is preferred for this step is toluene, dichloromethane or MTBE. The product of this reaction step is the azetidinone of formula (V). This compound is deprotected to bring back the ketone functionality. The deprotection may be carried out under acidic conditions and if desired the phenolic protecting group may also be removed at this stage.

In the next step, the ketone (VI) is reduced stereospecifically. Many such reductions are known and have been reported for the synthesis of the azetidinone (VIII). One such reduction is with chiral borane that is already disclosed in the product patent RE37721 and which the present inventors have used herein. The resulting alcohol (VII) is then subjected to a final deprotection of the phenolic group if it had not already been done before to yield the 1,4-diphenylazetidinone (VIII). This 1,4-diphenylazetidinone (VIII) that is obtained can be purified by crystallization or any other purification technique.

Needless to say, a person skilled in the art would contemplate different oxime protections for the ketone and different protecting groups for the phenolic —OH. This invention includes all such variations and procedural modifications. The process of the invention is further illustrated in the following examples. These examples are not to be construed to be limiting in any way.

Example 1

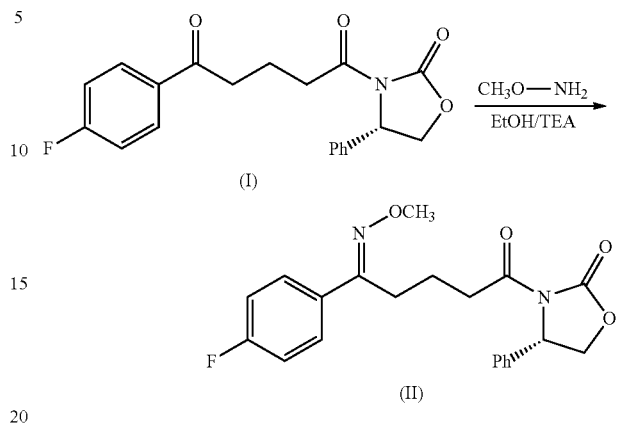

100 g of (4S)-3-[5-(4-fluorophenyl)-5-oxopentanoyl)]-4-phenyl-1,3-oxazolidin-2-one was added to 450 mL of denatured ethanol. To this solution was added 30.5 g of the hydrochloride salt of O-methyl hydroxylamine and 51.3 mL of triethylamine. This reaction mixture at room temperature was heated to 80-85° C. and maintained at this temperature for about 10 hrs. At this time the reaction was found to be complete and the reaction mixture was allowed to cool to 45-50° C. after which the solvent was distilled off under vacuum. The solid mass that was left behind was dissolved in 500 mL of dichloromethane and washed twice with water (200 mL). The organic solvent containing the product was concentrated to an oil and 400 mL of hexane was added to it. This mixture was stirred for about an hour and then filtered to give the title compound as a mixture of E and Z isomers (92.6:7.3), (95 g) m.p.: 73° C.

If desired the E and Z isomers may be separated from the mixture by column chromatography (e.g. silica gel, (60-120 mesh) with hexane-ethyl acetate 9:1 as the eluant). Identification of the isomers was done by NMR.

$^1$HNMR (DMSO-$d_6$ 200 MHz)

δ 7.85-7.55 (m, 2H), 7.50-7.10 (m, 7H), 5.45 (dd, J=3.01 and 5.34 Hz, 1H), 4.72 (t, J=8.66 Hz, 1H), 4.17 (dd, J=10.63 and 3.22 Hz, 1H), 3.87 (s, 3H), 2.91 (t, J=6.94 Hz, 2H), 2.71 (t, J=7.61 Hz, 2H), 1.67 (quintet, J=7.37 Hz, 2H).

MS=385.22 (M+1)

IR (KBr): 1781, 1765, 1702, 1512, 1396, 1331 cm$^{-1}$

Example 2

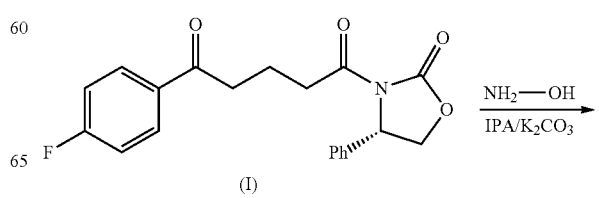

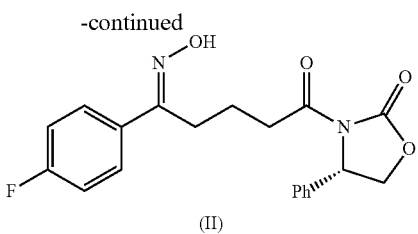

50 g of (4S)-3-[5-(4-fluorophenyl)-5-oxopentanoyl)]-4-phenyl-1,3-oxazolidin-2-one was added to 100 mL of isopropanol. To this solution was added 19.4 g of hydroxylamine hydrochloride and 58.4 g of anhydrous potassium carbonate. This reaction mixture at room temperature was heated to reflux and stirred at this temperature for about 2-4 hrs. At this time the reaction was found to be complete and the reaction mixture was allowed to cool to 45-50° C. after which the solvent was distilled off under vacuum. The solid mass that was left behind was washed with water and crystallized using 250 mL of isopropanol.

Example 3

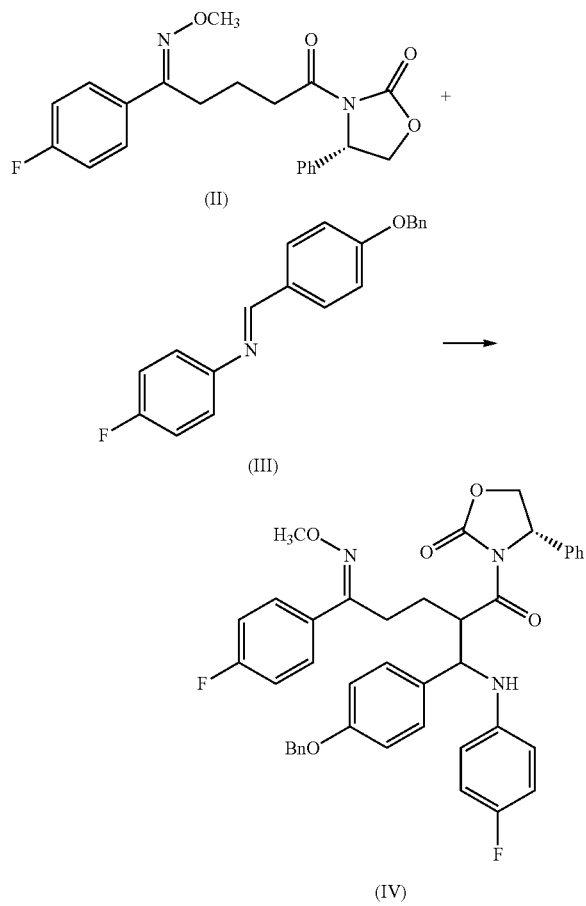

60 g of the oxime (product of Example 1) was dissolved in dichloromethane (120 mL). To this solution was added TiCl$_4$ (18.0 mL) and titanium isopropoxide (15.0 mL) in dichloromethane (780 mL) in an atmosphere of nitrogen. The reaction mixture was stirred for 30-40 min. at −5 to 0° C., diisopropylethylamine (58.5 mL) was added and stirring was continued for 1 hr at the same temperature. This was then cooled further to about −25° C. and 4-benzyloxybenzylidine-(4-fluoro)aniline (103.4 g) was added to it. The reaction mixture was stirred for another 5-6 hrs at the same temperature after which a mixture of acetic acid (60 mL) and dichloromethane (120 mL) was added dropwise over 20-25 min. This mixture was warmed to 0° C. and 2N H$_2$SO$_4$ (300 ml) was added dropwise over 20-25 min. The mixture was then warmed to 20-25° C. and stirring was continued for 1 hr, the layers were separated and the organic layer was washed with water (300 ml) and brine (20% soln., 300 ml). The solvent was distilled off u.v. to leave an oil which was crystallized from a mixture of ethyl acetate (240 ml) and n-heptane (1200 ml) to give a solid product (70 g). m.p.: 135-137° C.

$^1$H NMR (DMSO-d$_6$, 200 MHz)

δ 7.54-7.11 (m, 16H), 6.95-6.70 (m, 4H), 6.68-6.50 (m, 2H), 5.97 (d, 1H), 5.60 (dd, J=4.45 & 3.63, 1H), 5.02 (s, 2H), 4.78 (t, J=8.73, 1H), 4.48-4.30 (m, 2H), 4.20-4.08 (m, 1H), 3.83 (s, 3H), 2.85-2.52 (m, 3H), 1.67 (bs, 1H).

MS=690.94 (M+1)

IR (KBr): 3388, 1755, 1697, 1608, 1509, 1386 cm$^{-1}$

Example 4

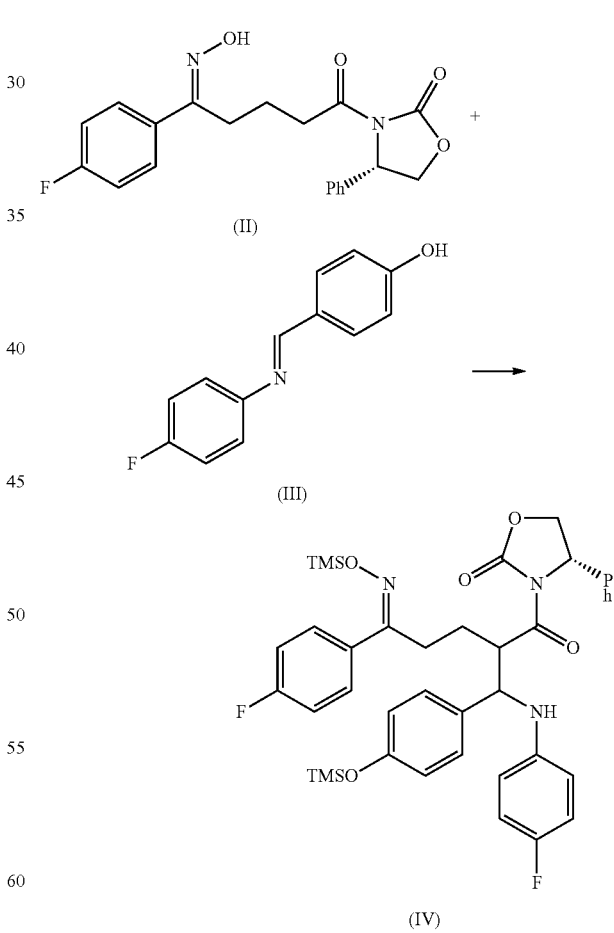

25 g of the oxime (product of Example 2) was dissolved in dichloromethane (375 mL) and the imine (III) (29 g) was added to it. The solution was cooled to −10 to −5° C. Diisopropylethyl amine (61.3 ml) was added slowly to this solution followed by trimethyl silyl chloride (28.5 ml). The temperature of the reaction medium was maintained at −10 to −5° C. and stirred till completion of the reaction. After completion of the reaction, the reaction mass was cooled to −30 to −25° C. and titanium tetrachloride (8.2 ml) was added slowly. The reaction mixture was stirred for 3-6 hrs at −30 to −25° C. After completion of the reaction glacial acetic acid was added to it at −20 to −25° C. The reaction mixture was quenched in 7% of tartaric acid solution (430 mL) at 0° C. and the temperature was raised to 25-30° C. The reaction mixture was stirred for 2-3 hrs at this temperature and 20% sodium bisulphate solution (125 ml) was added to it. Stirring was continued for 2-3 hrs at room temperature and then the dichloromethane layer was separated and washed with 125 ml of water. Dichloromethane was distilled out under vacuum completely and fresh dichloromethane was added. N,O-bis(trimethylsilyl)acetamide (BSA) 23.5 ml was added to the DCM solution, which was then refluxed for 1 hr. The DCM was recovered, a mixture of ethyl acetate (25 ml) and n-heptane (125 ml) was added to the reaction mass and stirred at room temperature for 1-2 hrs. The solid was filtered, washed with 25 ml of n-heptane and dried.

Example 5

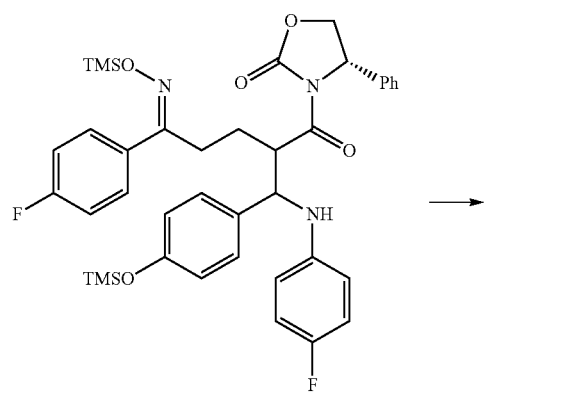

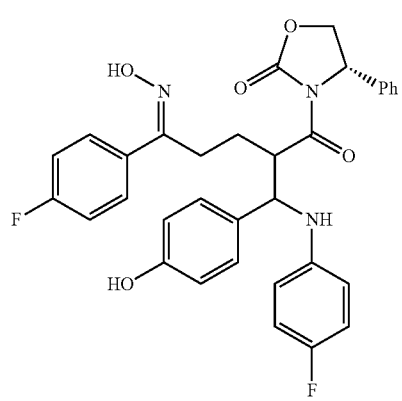

25 g of the product of example 4 was added to 325 ml methyl tertiary butyl ether. 30 ml of N,O-bis(trimethylsilyl) acetamide and TBAF solution in tetrahydrofuran (5 mole %) was added to it and the reaction mixture was stirred at room temperature for 2-4 hrs. After completion of the reaction, glacial acetic acid was added to it and the solvent was distilled off under vacuum to get an oil. 2N sulphuric acid (25 ml) and isopropyl alcohol (250 ml) were added to the above oil. The reaction mass was stirred at room temperature for 1-3 hrs. The solid was filtered, washed with 10 ml of IPA and dried.

Example 6

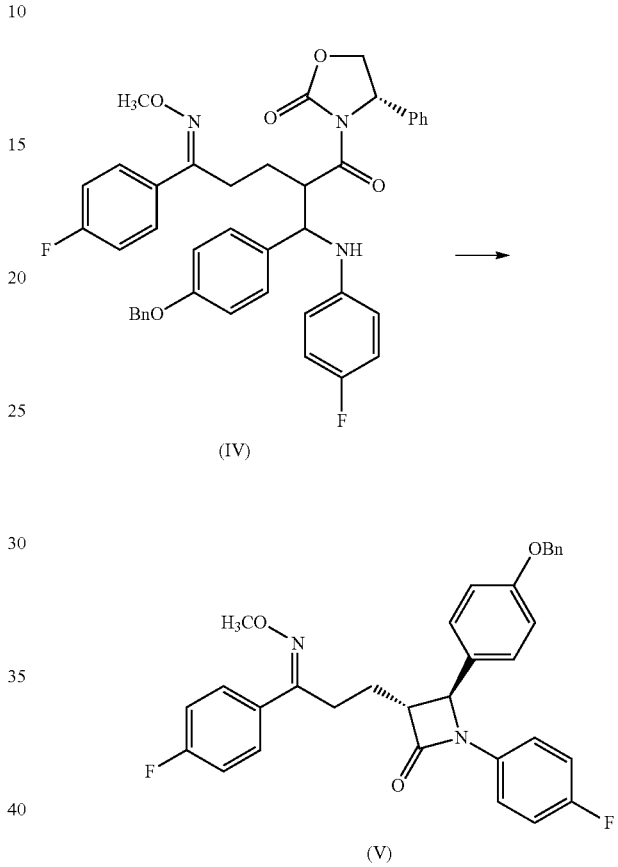

23 g of the product of example 3 was dissolved in toluene (345 mL) and warmed to 50° C. To this solution was added 46 mL of N,O-bis(trimethylsilyl)acetamide (BSA). The reaction mixture was stirred for 1 hr at 50° C. after which 3.35 g of tetrabutylammonium fluoride (1M in THF) was added. After 4 hrs the reaction mixture was cooled to 15-20° C., 25 mL of MeOH was added to it followed by 46 mL of 1N HCl, the layers were separated and the organic layer was washed with water (92 mL) and brine (20%, 92 mL). The solvent was distilled off u.v. to leave an oil that was purified by flash chromatography to afford a liquid product. (15 g) b.p.: 105° C.

$^1$H NMR (200 MHz) in CDCl$_3$

δ7.67-7.60 (m, 2H), 7.44-7.23 (m, 10H), 7.10-6.91 (m, 6H), 5.10 (s, 2H) 4.63 (d, J=2.0, 1H), 3.90 (s, 3H), 3.20 (t, J=6.20, 1H), 2.93 (t, J=7.8, 2H), 2.14 (m, 2H)

Mass spectra 527.11 (M+1)

IR (KBr): 2924, 1745, 1610, 1585, 1506 cm$^{-1}$

Example 7

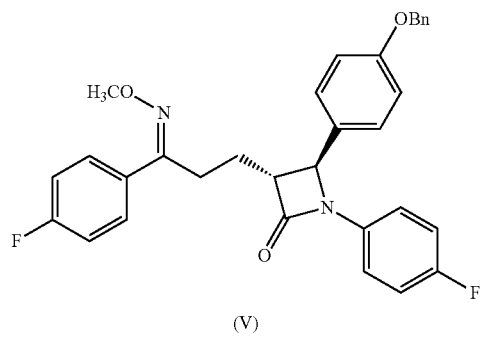

(V)

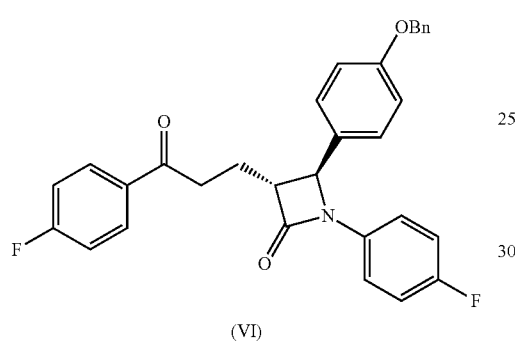

(VI)

500 g of the product obtained in example 6 was dissolved in a mixture of acetone and 1,4-dioxane (1:1, 10 mL). 5M HCl (1 mL) was added to it and the reaction mixture was heated for 6 hrs at 90-95° C. The reaction mixture was cooled to 45-50° C. and the solvent was distilled off u.v. to give an oil that was dissolved in dichloromethane, washed with water (2 mL) and brine (10%, 2 mL). Again solvent was distilled off and the resulting oil was purified by flash chromatography.

Example 8

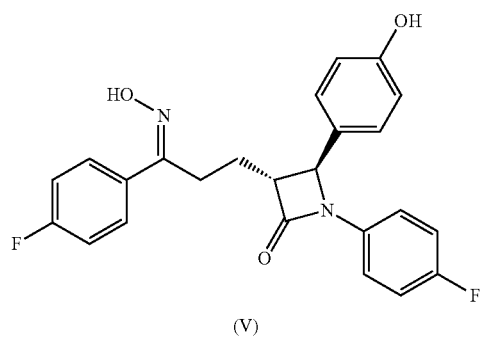

(V)

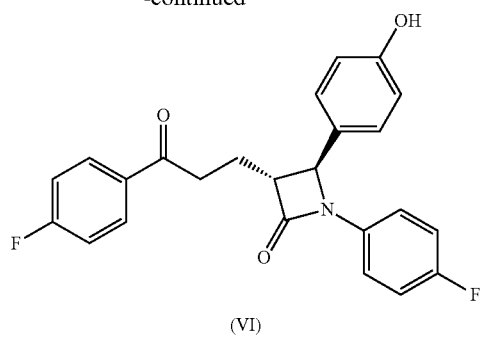

(VI)

To a 20 ml solution of ethanol and water (1:1) was added 2 g of compound of formula (V). 0.85 ml of formic acid was added to it followed by sodium bisulphate (3.4 g). The reaction mixture was refluxed for 2-4 hrs. After completion of the reaction, the solvent was distilled off and the reaction mass was extracted with ethyl acetate. Ethyl acetate was then distilled off to yield the product.

Example 9

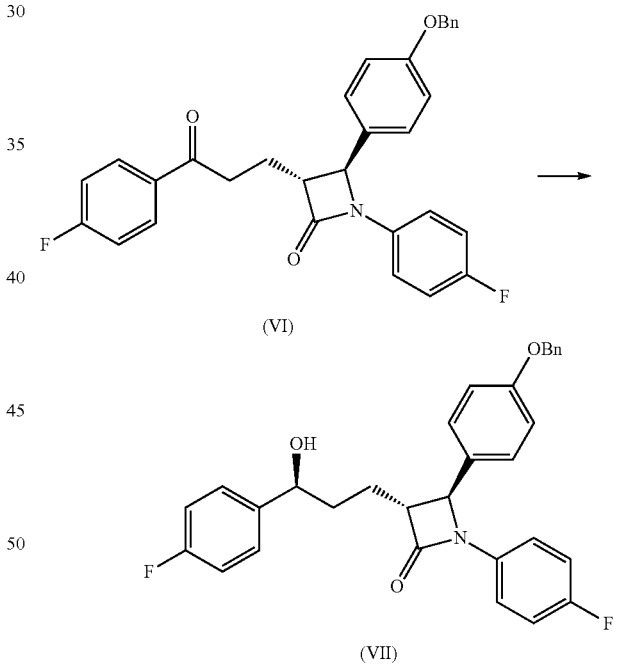

Borane-dimethylsulfide complex in THF (0.5 mL, 5.2 mmole) was cooled to about −10° C. and (R)-tetrahydro-1-methyl-3,3-diphenyl-1H,3H-pyrrolo[1,2-C][1,3,2]ox-azaborolidine (0.2 mL, 1M in toluene) was added to it slowly. After stirring for 15-20 min. the ketone (VI) (2 g) was added to it and the reaction mixture was stirred for another 3 hrs at 0-5° C. The reaction was quenched with MeOH (2 mL) and 1N HCl (5 mL) was added after 0.5 hr. After stirring for another 0.5 hr at 5-10° C., the product was extracted with ethyl acetate (50 mL). This solution as washed with brine (20 ml×2) and concentrated to an oil, which was purified by flash chromatography.

Example 10

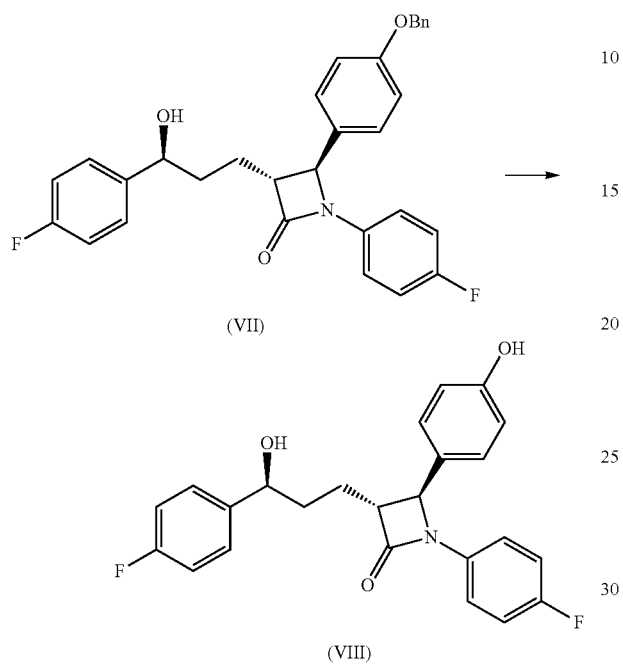

1 g of the alcohol (VII) was taken in MeOH (25 mL) and ammonium formate (1.5 g) and 10% Pd/C (150 g) was added to it. The pH was adjusted to 3-4 with glacial acetic acid (2 mL) and the reaction mixture was warmed to 55-60° C. After stirring it at this temperature under nitrogen for 3 hrs, the mixture was filtered through celite. The filtrate was concentrated to an oil, which was added to a mixture of ethyl acetate (25 mL) and water (10 mL). The organic layer was separated, washed with brine (20%, 5 mL×2) and distilled off. The oil obtained was crystallized with aq. EtOH and re-crystallized with isopropanol-water.

The invention claimed is:

1. A process for the preparation of the compound of formula (VIII),

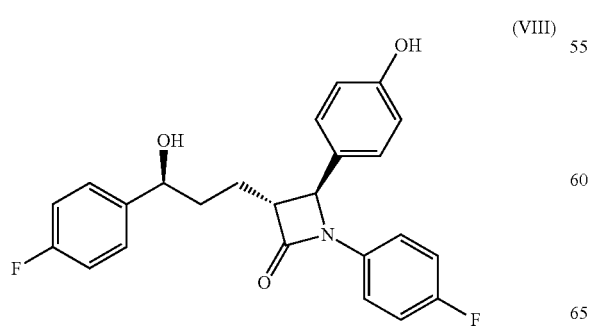

the process comprising the steps of a) reacting hydroxylamine or its derivative with a ketone of formula (I) to obtain an oxime of formula (II) wherein R=H, alkyl or silyl;

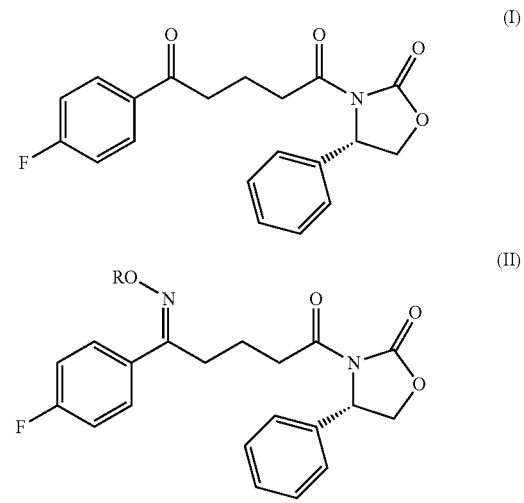

b) reacting the oxime of formula (II) with an imine of formula (III), wherein R'=H or any phenolic protecting group to obtain β-(substituted-amino)amide of formula (IV);

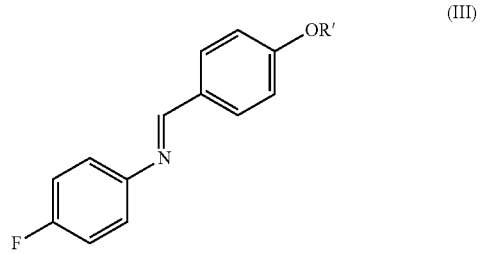

c) cyclizing the β-(substituted-amino)amide of formula (IV) to form an azetidinone of formula (V);

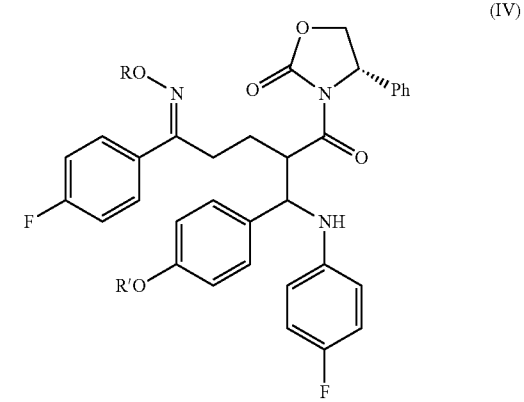

the process comprising the steps of a) reacting the oxime of formula (II), wherein R=H, alkyl or silyl; with an imine of formula (III), wherein R'=H or any phenolic protecting group to obtain β-(substituted-amino)amide of formula (IV);

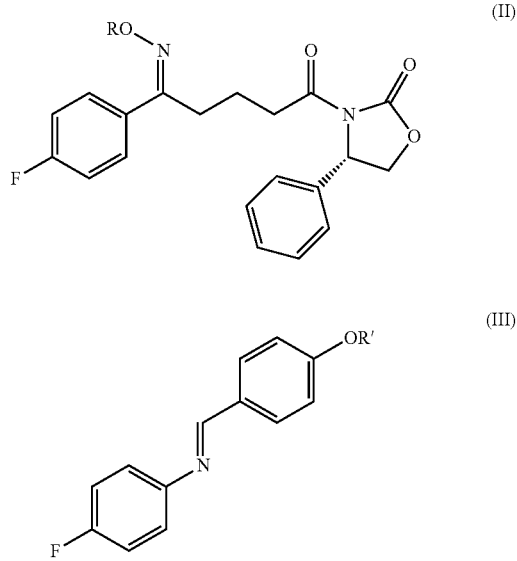

b) cyclizing the β-(substituted-amino)amide of formula (IV) to form an azetidinone of formula (V);

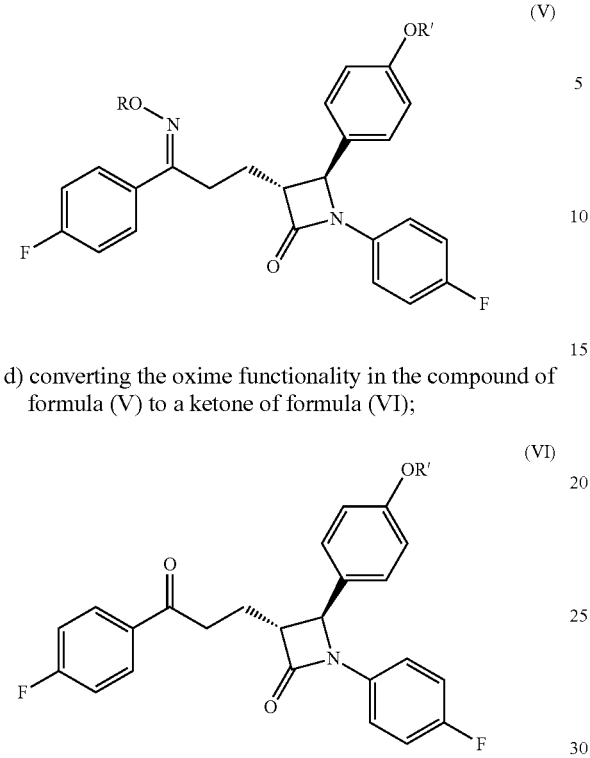

c) converting the oxime functionality in the compound of formula (V) to a ketone of formula (VI);

d) converting the oxime functionality in the compound of formula (V) to a ketone of formula (VI);

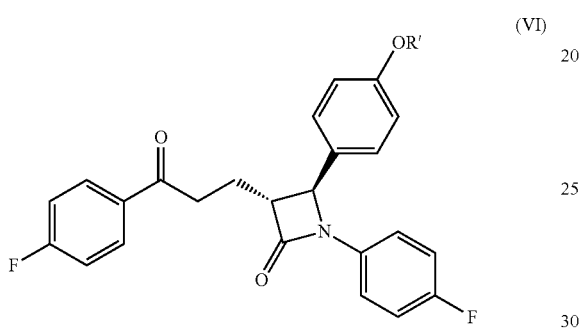

e) reducing the ketone functionality of a compound of formula (VI) to the alcohol of formula (VII);

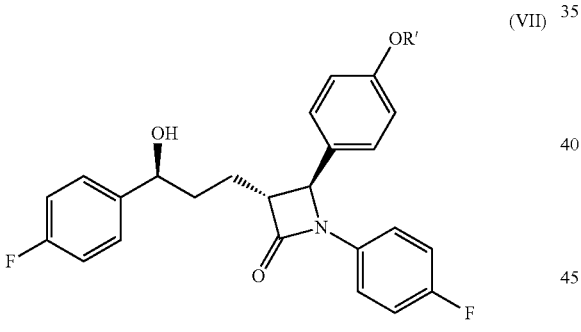

f) removing the phenolic protecting group at any desired stage in the above synthesis.

2. A process for the preparation of the compound of formula (VIII),

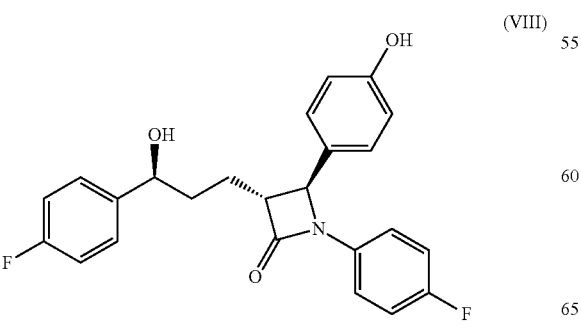

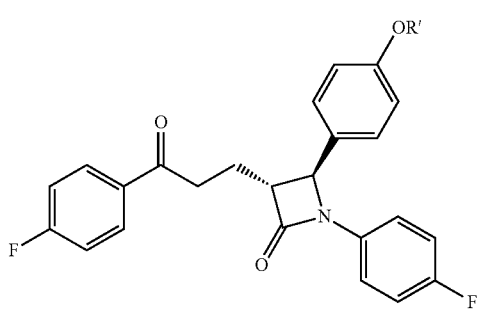
(VI)

d) reducing the ketone functionality of a compound of formula (VI) to the alcohol of formula (VII);

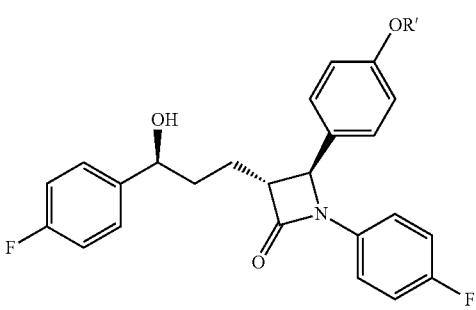
(VII)

e) removing the phenolic protecting group at any desired stage in the above synthesis.

3. A process for the preparation of the compound of formula (VIII),

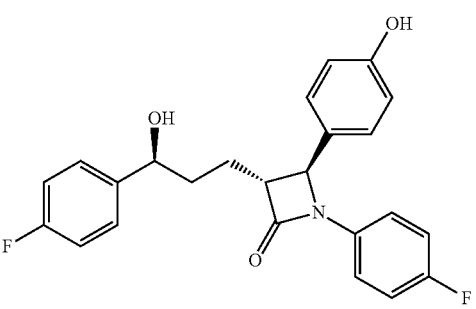
(VIII)

the process comprising the steps of a) cyclizing the β-(substituted-amino)amide of formula (IV), wherein R=H, alkyl or silyl and R'=H or any phenolic protecting group, to form an azetidinone of formula (V);

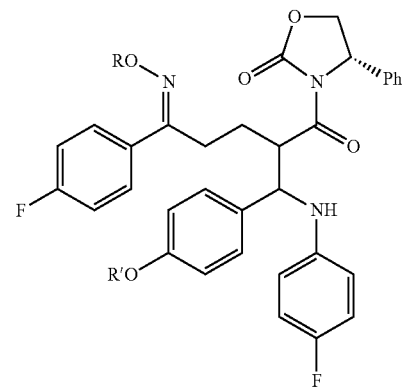
(IV)

(V)

b) converting the oxime functionality in the compound of formula (V) to a ketone of formula (VI);

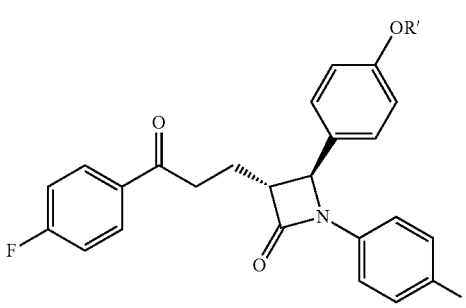
(VI)

c) reducing the ketone functionality of a compound of formula (VI) to the alcohol of formula (VII);

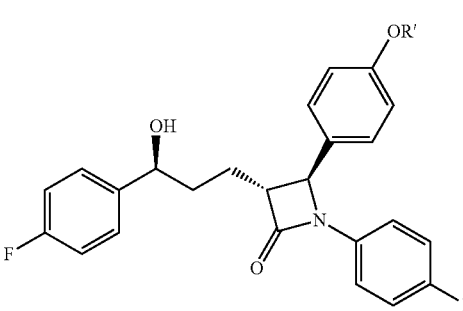
(VII)

d) removing the phenolic protecting group at any desired stage in the above synthesis.

4. A process for the preparation of the compound of formula (VIII),

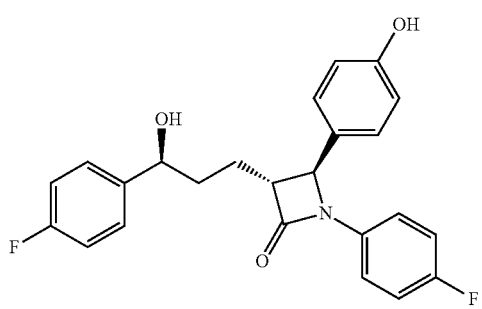
(VIII)

the process comprising the steps of
a) converting the oxime of formula (V), wherein R=H, alkyl or silyl and R'=H or any phenolic protecting group, to a ketone of formula (VI);

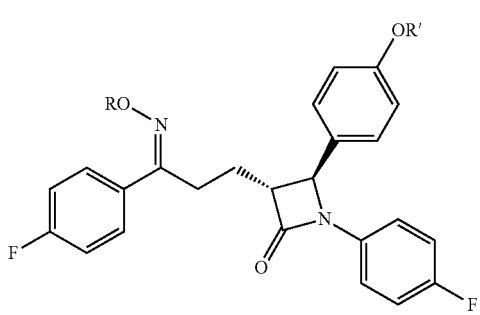
(V)

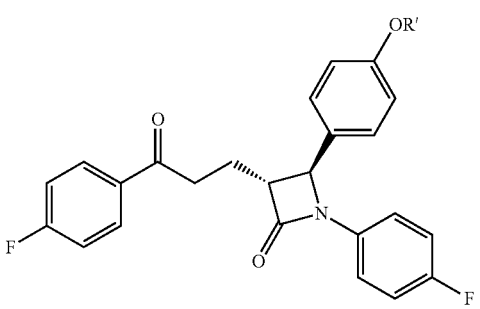
(VI)

b) reducing the ketone functionality of a compound of formula (VI) to the alcohol of formula (VII);

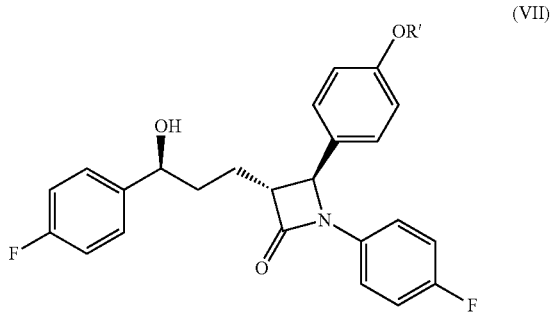
(VII)

removing the phenolic protecting group at any desired stage in the above synthesis.

5. The process according to claim 1 wherein the hydroxylamine or its derivative that is used in step a) is for protecting the ketone functionality; wherein the cyclization of step c) is carried out in the presence of a silylating agent; wherein converting oxime compound to ketone compound of step d) is carried out in the presence of an acid; and wherein the reduction of step e) is carried out stereo specifically.

6. The process according to claim 2 wherein the cyclization of step b) is carried out in the presence of a silylating agent; wherein converting oxime compound to ketone compound of step c) is carried out in the presence of an acid; and wherein the reduction of step d) is carried out stereo specifically.

7. A process according to claim 3 wherein the cyclization of step a) is carried out in the presence of a silylating agent; wherein converting oxime compound to ketone compound of step b) is carried out in the presence of an acid; and wherein the reduction of step c) is carried out stereo specifically.

8. A process according to claim 4 wherein converting oxime compound to ketone compound of step a) is carried out in the presence of an acid; and wherein the reduction of step b) is carried out stereo specifically.

9. A process according to claim 1 wherein hydroxylamine is used to protect the ketone functionality.

* * * * *